(12) United States Patent
Wong et al.

(10) Patent No.: US 9,932,559 B2
(45) Date of Patent: Apr. 3, 2018

(54) PLATFORM FOR CREATING AN ARTIFICIAL BLOOD BRAIN BARRIER

(71) Applicant: The Johns Hopkins University, Baltimore, MD (US)

(72) Inventors: Andrew D. Wong, Baltimore, MD (US); Peter C. Searson, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 1392 days.

(21) Appl. No.: 13/679,510

(22) Filed: Nov. 16, 2012

(65) Prior Publication Data

US 2014/0142370 A1 May 22, 2014

(51) Int. Cl.
| | |
|---|---|
| *C12N 5/071* | (2010.01) |
| *C12M 1/12* | (2006.01) |
| *C12N 5/00* | (2006.01) |
| *C12M 3/00* | (2006.01) |
| *C12M 1/00* | (2006.01) |
| *A61F 2/06* | (2013.01) |

(52) U.S. Cl.
CPC ............ *C12N 5/0691* (2013.01); *C12M 21/08* (2013.01); *C12M 25/10* (2013.01); *C12M 25/14* (2013.01); *C12M 29/10* (2013.01); *C12N 5/0068* (2013.01); *C12N 5/069* (2013.01); *A61F 2/062* (2013.01); *C12N 2533/30* (2013.01); *C12N 2533/90* (2013.01)

(58) Field of Classification Search
CPC ....... A61F 2/062; C12N 5/069; C12N 5/0691; C12N 25/10; C12N 25/14; C12N 2513/00; C12M 21/08
See application file for complete search history.

(56) References Cited

U.S. PATENT DOCUMENTS

| | | | | |
|---|---|---|---|---|
| 2,694,033 A | * | 11/1954 | Fletcher | C12M 23/10 435/305.1 |
| 5,863,531 A | * | 1/1999 | Naughton | A61B 19/00 424/423 |
| 7,371,400 B2 | * | 5/2008 | Borenstein | A61L 27/3604 424/423 |
| 7,393,437 B2 | * | 7/2008 | Chan | A61L 27/24 204/157.61 |
| 2002/0142459 A1 | * | 10/2002 | Williams | C12N 5/0691 435/366 |
| 2005/0260745 A1 | * | 11/2005 | Domansky | C12M 29/10 435/294.1 |
| 2007/0088114 A1 | * | 4/2007 | Asgari | A61K 9/1664 524/431 |

(Continued)

OTHER PUBLICATIONS

Belayev, L., Busto, R., Zhao, W. & Ginsberg, M. D. Quantitative evaluation of blood-brain barrier permeability following middle cerebral artery occlusion in rats. Brain Res 739, 88-96, (1996).

(Continued)

*Primary Examiner* — Charles A Marmor, II
*Assistant Examiner* — Carrie R Dorna
(74) *Attorney, Agent, or Firm* — Michael Best & Friedrich, LLP; Jeffrey W. Childers

(57) ABSTRACT

A platform for creating an artificial blood brain barrier including a functional, perfused artificial vessel lined with endothelial cells embedded in a physiologically relevant three-dimensional extracellular matrix is described.

12 Claims, 7 Drawing Sheets

(56) References Cited

U.S. PATENT DOCUMENTS

| | | | | |
|---|---|---|---|---|
| 2007/0224677 A1* | 9/2007 | Neumann | | C12M 21/08 435/325 |
| 2010/0273200 A1* | 10/2010 | Niwa | | C12M 35/08 435/29 |
| 2011/0104658 A1* | 5/2011 | Prabhakarpandian | | G01N 33/5029 435/5 |
| 2013/0288375 A1* | 10/2013 | Zhang | | C12N 5/0068 435/397 |

OTHER PUBLICATIONS

Lo, E. H., Dalkara, T. & Moskowitz, M. A. Mechanisms, challenges and opportunities in stroke. Nat Rev Neurosci 4, 399-415, (2003).

Lippoldt, A. et al. Structural alterations of tight junctions are associated with 5 loss of polarity in stroke-prone spontaneously hypertensive rat blood-brain barrier endothelial cells. Brain Res 885, 251-261 (2000).

del Zoppo, G. J. The neurovascular unit in the setting of stroke. J Intern Med 267, 156-171(2010).

Remy, S. & Beck, H. Molecular and cellular mechanisms of pharmacoresistance in epilepsy. Brain 129, 18-35, (2006).

Oby, E. & Janigro, D. The blood-brain barrier and epilepsy. Epilepsia 47, 1761-1774, (2006).

Seiffert, E. et al. Lasting blood-brain barrier disruption induces epileptic focus in the rat somatosensory cortex. Journal of Neuroscience 24, 7829-7836, (2004).

Berger, J. R. & Avison, M. The blood brain barrier in HIV infection. Front Biosci 9, 2680-2685, (2004).

Dallasta, L. M. et al. Blood-brain barrier tight junction disruption in human immunodeficiency virus-I encephalitis. Am J Patrol 155, 1915-1927, (1999).

Persidsky, Y. et al. Rho-mediated regulation of tight junctions during monocyte migration across the blood-brain barrier in HIV-I encephalitis (HIVE). Blood 107, 4770-4780, (2006).

Uchiyama, S. et al. The surface-anchored NanA protein promotes 25 pneumococcal brain endothelial cell invasion. J Exp Med 206, 1845-1852, (2009).

Minagar, A. & Alexander, J. S. Blood-brain barrier disruption in multiple sclerosis. Mult Scler 9, 540-549 (2003).

McQuaid, S., Cunnea, P., McMahon, J. & Fitzgerald, U. The effects of blood-brain barrier disruption on glial cell function in multiple sclerosis. Biochem Soc Trans 37, 329-331, (2009).

Gold, R., Linington, C. & Lassmann, H. Understanding pathogenesis and therapy of multiple sclerosis via animal models: 70 years of merits and culprits in experimental autoimmune encephalomyelitis research. Brain 129, 1953-1971, (2006).

Waubant, E. Biomarkers indicative of blood-brain barrier disruption in multiple sclerosis. Dis Markers 22, 235-244 (2006).

Kermode, A. G. et al. Breakdown of the Blood-Brain-Barrier Precedes Symptoms and Other Mri Signs of New Lesions in Multiple-Sclerosis—Pathogenetic and Clinical Implications. Brain 113, 1477-1489 (1990).

Bronger, H. et al. ABCC drug efflux pumps and organic anion uptake transporters in human gliomas and the blood-tumor barrier. Cancer Res 65, 11419-11428, (2005).

Papadopoulos, M. C. et al. Molecular mechanisms of brain tumor edema. Neuroscience 129, 1011-1020, (2004).

Davies, D. C. Blood-brain barrier breakdown in septic encephalopathy and brain tumours. J Anat 200, 639-646 (2002).

Stahel, P. F. et al. Experimental closed head injury: analysis of neurological outcome, blood-brain barrier dysfunction, intracranial neutrophil infiltration, and neuronal cell death in mice deficient in genes for pro-inflammatory cytokines. J Cereb Blood Flow Metab 20, 369-380, (2000).

Kim, J. V. & Dustin, M. L. Innate response to focal necrotic injury inside the blood-brain barrier. J Immunol 177, 5269-5277 (2006).

Shlosberg, D., Benifla, M., Kaufer, D. & Friedman, A. Blood-brain barrier breakdown as a therapeutic target in traumatic brain injury. Nat Rev Neurol 6, 393-403, (2010).

Nakagawa, S. et al. A new blood-brain barrier model using primary rat brain endothelial cells, pericytes and astrocytes. Neurochem Int 54, 253-263, (2009).

Zozulya, A., Weidenfeller, C. & Galla, H. J. Pericyte-endothelial cell interaction increases MMP-9 secretion at the blood-brain barrier in vitro. Brain Res 1189, 1-11, (2008).

Weidenfeller, C., Svendsen, C. N. & Shusta, E. V. Differentiating embryonic neural progenitor cells induce blood-brain barrier properties. J Neurochem 101, 555-565, (2007).

Tilling, T., Korte, D., Hoheisel, D. & Galla, H. J. Basement membrane proteins influence brain capillary endothelial barrier function in vitro. J Neurochem 71, 1151-1157 (1998).

Rubin, L. L. et al. A Cell-Culture Model of the Blood-Brain-Barrier. Journal of Cell Biology 115, 1725-1735 (1991).

Bickel, U. How to measure drug transport across the blood brain barrier. NeuroRX 2, 15-26 (2005).

Ma, S. H., Lepak, L. A., Hussain, R. J., Shain, W. & Shuler, M. L. An endothelial and astrocyte co-culture model of the blood-brain barrier utilizing an ultra-thin, nanofabricated silicon nitride membrane. Lab Chip 5, 74-85 (2005).

Siddharthan, V., Kim, Y. V., Liu, S. & Kim, K. S. Human astrocytes/astrocyte-conditioned medium and shear stress enhance the barrier properties of human brain microvascular endothelial cells. Brain Research 1147, 39-50, (2007).

Lundquist, S. & Renftel, M. The use of in vitro cell culture models for mechanistic studies and as permeability screens for the blood-brain barrier in the pharmaceutical industry—Background and current status in the drug discovery process. Vase Pharmacol 38, 355-364 (2002).

Lundquist, S. et al. Prediction of drug transport through the blood-brain barrier in vivo: A comparison between two in vitro cell models. Pharmaceut Res 19, 976-981 (2002).

Stanness, K. A. et al. Morphological and functional characterization of an in vitro blood-brain barrier model. Brain research 771, 329-342 (1997).

Cucullo, L. et al. Development of a humanized in vitro blood-brain barrier model to screen for brain penetration of antiepileptic drugs. Epilepsia 48, 505-516, (2007).

Griffith, L. G. & Swartz, M. A. Capturing complex 3D tissue physiology in vitro. Nature reviews. Molecular cell biology 7, 211-224, (2006).

Armstrong, J. K., Wenby, R. B., Meiselman, H. J. & Fisher, T. C. The hydrodynamic radii of macromolecules and their effect on red blood cell aggregation. Biophys J 87, 4259-4270, (2004).

Bouis, D., Hospers, G. A., Meijer, C., Molema, G. & Mulder, N. H. Endothelium in vitro: a review of human vascular endothelial cell lines for blood vessel-related research. Angiogenesis 4, 91-102 (2001).

Poller, B. et al. The human brain endothelial cell line hCMEC/D3 as a human blood-brain barrier model for drug transport studies. Journal of neurochemistry 107, 1358-1368 (2008).

Weksler, B. B. et al. Blood-brain barrier-specific properties of a human adult brain endothelial cell line. Faseb J 19, 1872-1874, (2005).

Hawkins, B. T. & Davis, T. P. The blood-brain barrier/neurovascular unit in health and disease. Pharmacological reviews 57, 173-185, (2005).

Hirst, D. G., Denekamp, J. & Hobson, B. Proliferation Studies of the Endothelial and Smooth-Muscle Cells of the Mouse Mesentery after Irradiation. Cell Tissue Kinet 13, 91-104 (1980).

Wright, H. P. Mitosis Patterns in Aortic Endothelium. Atherosclerosis 15, 93-100 (1972).

Chrobak, K. M., Potter, D. R. & Tien, J. Formation of perfused, functional microvascular tubes in vitro. Microvasc Res 71, 185-196, (2006).

Yuan, Y., Chilian, W. M., Granger, H. J. & Zawieja, D. C. Permeability to albumin in isolated coronary venules. Am J Physiol 265, H543-552 (1993).

(56) References Cited

OTHER PUBLICATIONS

Huxley, V. H., Curry, F. E. & Adamson, R. H. Quantitative Fluorescence Microscopy on Single Capillaries—Alpha-Lactalbumin Transport. Am J Physiol 252, H188-H197 (1987).

Price, G. M., Chrobak, K. M. & Tien, J. Effect of cyclic AMP on barrier function of human lymphatic microvascular tubes. Microvasc Res 76, 46-51, (2008).

Vlodaysky, I., Lui, G. M. & Gospodarowicz, D. Morphological appearance, growth behavior and migratory activity of human tumor cells maintained on extracellular matrix versus plastic. Cell 19, 607-616 (1980).

Zheng, Y. et al. In vitro microvessels for the study of angiogenesis and thrombosis. Proc Natl Acad Sci U S A 109, 9342-9347, (2012).

Wong, K.H.K., Truslow, J.G., and Tien, J. The role of cyclic AMP in normalizing the function of engineered human blood microvessels in microfluidic collagen gels. Biomaterials 31(17), 4706-4714 (2010).

Abbott, N. J., Patabendige, A. A., Dolman, D. E., Yusof, S. R. & Begley, D. J. Structure and function of the blood-brain barrier. Neurobiol Dis 37, 13-25, (2010).

Neuwelt, E. A. et al. Engaging neuroscience to advance translational research in brain barrier biology. Nat Rev Neurosci 12, 169-182, (2011).

Cecchelli, R. et al. Modelling of the blood-brain barrier in drug discovery and 5 development. Nat Rev Drug Discov 6, 650-661 (2007).

Neuwelt, E. et al. Strategies to advance translational research into brain barriers. Lancet Neurol 7, 84-96 (2008).

Begley, D. J. & Brightman, M. W. in Progress in Drug Research vol. 61 (ed L. Prokai and K. Prokai-Tatrai) 39-78 (Birkhauser Verlag, 2003).

Ohtsuki, S. & Terasaki, T. Contribution of carrier-mediated transport systems to the blood-brain barrier as a supporting and protecting interface for the brain; Importance for CNS drug discovery and development. Pharmaceut Res 24, 1745-1758, (2007).

Ueno, M. Mechanisms of the Penetration of Blood-Borne Substances into the Brain. Curr Neuropharmacol 7, 142-149 (2009).

Hartz, A. M. & Bauer, B. ABC transporters in the CNS—an inventory. Curr 20 Pharm Biotechnol 12, 656-673, (2011).

Hawkins, R. A., Peterson, D. R. & Vina, J. R. The complementary membranes forming the blood-brain barrier. IUBMB Life 54, 101-107, (2002).

Chishty, M., Reichel, A., Siva, J., Abbott, N. J. & Begley, D. J. Affinity for the P-glycoprotein efflux pump at the blood-brain barrier may explain the lack of CNS side-effects of modern antihistamines. J Drug Target 9, 223-228 (2001).

Demeule, M. et al. Drug transport to the brain: Key roles for the efflux pump P-glycoprotein in the blood-brain barrier. Vase Pharmacol 38, 339-348, (2002).

Debault, L. E. & Cancilla, P. A. Gamma-Glutamyl-Transferase Transpeptidase in Isolated Brain Endothelial-Cells—Induction by Glial-Cells Invitro. Science 207, 653-655 (1980).

Janzer, R. C. & Raff, M. C. Astrocytes induce blood brain barrier properties in endothelial cells. Nature 325, 253-257 (1987).

Abbott, N. J. Astrocyte-endothelial interactions and blood-brain barrier permeability. J Anat 200, 629-638 (2002).

Abbott, N. J., Ronnback, L. & Hansson, E. Astrocyte-endothelial interactions at the blood-brain barrier. Nat Rev Neurosci 7, 41-53 (2006).

Haseloff, R. F., Blasig, I. E., Bauer, H. C. & Bauer, H. In search of the astrocytic factor(s) modulating blood-brain barrier functions in brain capillary endothelial cells in vitro. Cell Mol Neurobiol 25, 25-39 (2005).

Armulik, A., Abramsson, A. & Betsholtz, C. Endothelial/pericyte interactions. Circ Res 97, 512-523, (2005).

Hammes, H. P. et al. Pericytes and the pathogenesis of diabetic retinopathy. Diabetes 51, 3107-3112 (2002).

Hellstrom, M. et al. Lack of pericytes leads to endothelial hyperplasia and abnormal vascular morphogenesis. Journal of Cell Biology 153, 543-553 (2001).

Fisher, M. Pericyte signaling in the neurovascular unit. Stroke 40, S 13-15, 15 (2009).

Bell, R. D. et al. Pericytes control key neurovascular functions and neuronal phenotype in the adult brain and during brain aging. Neuron 68, 409-427, (2010).

Armulik, A. et al. Pericytes regulate the blood-brain barrier. Nature 468, 557-20 561, (2010).

Daneman, R., Zhou, L., Kebede, A. A. & Barres, B. A. Pericytes are required for blood-brain barrier integrity during embryogenesis. Nature 468, 562-566, (2010).

Winkler, E. A., Bell, R. D. & Zlokovic, B. V. Central nervous system pericytes in health and disease. Nature Neuroscience 14, 1398-1405, (2011).

Bonkowski, D., Katyshev, V., Balabanov, R. D., Borisov, A. & Dore-Duffy, P. The CNS microvascular pericyte: pericyte-astrocyte crosstalk in the regulation of tissue survival. Fluids Barriers CNS 8, 8, (2011).

Tilling, T. et al. Expression and adhesive properties of basement membrane proteins in cerebral capillary endothelial cell cultures. Cell Tissue Res 310, 19-29, (2002).

Hartmann, C., Zozulya, A., Wegener, J. & Galla, H. J. The impact of glia-derived extracellular matrices on the barrier function of cerebral endothelial cells: an in vitro study. Exp Cell Res 313, 1318-1325, (2007).

Cunningham, L. A., Wetzel, M. & Rosenberg, G. A. Multiple roles for MMPs 5 and TIMPs in cerebral ischemia. Glia 50, 329-339, (2005).

Tarbell, J. M. Shear stress and the endothelial transport barrier. Cardiovasc Res 87, 320-330, doi:cvq146 (2010).

Krizanac-Bengez, L., Mayberg, M. R. & Janigro, D. The cerebral vasculature as a therapeutic target for neurological disorders and the role of shear stress in vascular homeostatis and pathophysiology. Neurol Res 26, 846-853, (2004).

Cucullo, L., Hossain, M., Puvenna, V., Marchi, N. & Janigro, D. The role of shear stress in blood-brain barrier endothelial physiology. BMC Neuroscience 12, (2011).

Pardridge, W. M. Blood-brain barrier drug targeting: the future of brain drug development. Mol Interv 3, 90-105 (2003).

Pardridge, W. M. The blood-brain barrier: bottleneck in brain drug development. NeuroRx 2, 3-14 (2005).

Pardridge, W. M. Molecular Trojan horses for blood-brain barrier drug delivery. Curr Opin Pharmacol 6, 494-500 (2006).

Pardridge, W. M. Biopharmaceutical drug targeting to the brain. J Drug Target 18, 157-167, (2010).

Pardridge, W. M. Re-engineering biopharmaceuticals for delivery to brain with molecular Trojan horses. Bioconjugate Chem 19, 1327-1338, (2008).

Thepharmaletter. Global CNS market set to decline, but will see launch of multiple anti-Alzheimer's drugs in Japan. (2010).

Engelhardt, B. Immune cell entry into the central nervous system: Involvement of adhesion molecules and chemokines. J Neurol Sci 274, 23-26, (2008).

Engelhardt, B. The blood-central nervous system barriers actively control immune cell entry into the central nervous system. Curr Pharm Design 14, 1555-1565 (2008).

Zlokovic, B. V. Neurovascular mechanisms of Alzheimer's neurodegeneration. 5 Trends Neurosci 28, 202-208, (2005).

Kalaria, R. N. The blood-brain barrier and cerebrovascular pathology in Alzheimer's disease. Ann N Y Acad Sci 893, 113-125 (1999).

Zipser, B. D. et al. Microvascular injury and blood-brain barrier leakage in Alzheimer's disease. Neurobiology of Aging 28, 977-986, (2007).

Meyer, E. P., Ulmann-Schuler, A., Staufenbiel, M. & Krucker, T. Altered morphology and 3D architecture of brain vasculature in a mouse model for Alzheimer's disease. P Natl Acad Sci USA 105, 3587-3592, (2008).

Hartz, A. M., Miller, D. S. & Bauer, B. Restoring blood-brain barrier P-glycoprotein reduces brain amyloid-beta in a mouse model of Alzheimer's disease. Mol Pharmacol 77, 715-723, (2010).

Desai, B. S., Monahan, A. J., Carvey, P. M. & Hendey, B. Blood-brain barrier pathology in Alzheimer's and Parkinson's disease: implications for drug therapy. Cell Transplant 16, 285-299 (2007).

(56) References Cited

OTHER PUBLICATIONS

Zhong, Z. et al. ALS-causing SOD 1 mutants generate vascular changes prior to motor neuron degeneration. Nat Neurosci 11, 420-422, (2008).
Bartels, A. L. et al. Decreased blood-brain barrier P-glycoprotein function in the progression of Parkinson's disease, PSP and MSA. J Neural Transm 115, 1001-25 1009, (2008).
Kortekaas, R. et al. Blood-brain barrier dysfunction in parkinsonian midbrain in vivo. Ann Neurol 57, 176-179, (2005).
Moskowitz, M. A., Lo, E. H. & Iadecola, C. The science of stroke: mechanisms in search of treatments. Neuron 67, 181-198, (2010).

\* cited by examiner a b

PLATFORM FOR CREATING AN ARTIFICIAL BLOOD BRAIN BARRIER

BACKGROUND

The blood-brain barrier is a complex dynamic interface that transduces biomechanical and biochemical signals from the vascular system and the brain and is responsible for maintaining homeostasis of the brain by regulating exchange of water, ions, nutrients, metabolites, neurotransmitters, and other cells (e.g., leukocytes), while limiting entry of potentially toxic xenobiotics in the blood (Abbott et al., 2010; Hawkins and Davis, 2005; Begley and Brightman, 2003).

The BBB is formed, in part, by highly specialized endothelial cells that line brain capillaries. The tight junctions formed by brain microvascular endothelial cells (BMECs) regulate paracellular transport, whereas transcellular transport is regulated by specialized transporters, pumps, and receptors (Abbott et al., 2010; Ohtsuki and Terasaki, 2007; Ueno, 2009; Hartz and Bauer, 2011; Hawkins et al., 2002; Chishty et al., 2001; Demeule et al., 2002). This barrier regulates transport by transducing signals from the vascular system and the central nervous system. Mounting evidence indicates that the structure and function of the BBB is controlled by the complex interplay between BMECs, astrocytes, pericytes, basement membrane proteins, components of the blood, and the shear stress associated with blood flow.

In 1980, it was shown that co-culture of brain capillary endothelial cells and astrocytes was essential to maintaining several important features of the BBB (Debault and Cancilla, 1980). Strong evidence indicates that astrocytes upregulate many BBB features leading to the formation of improved tight junctions, the expression and polarized localization of transporters to the apical or basal membranes, and specialized enzyme systems (Debault and Cancilla, 1980; Janzer and Raff, 1987; Abbott, 2002; Abbott et al., 2006; Haseloff et al., 2005).

The lack of a physiologically relevant in vitro model system, however, has been identified as a significant barrier to progress in this field. (Neuwelt et al., 2011; Cecchelli et al., 2007; Neuwelt et al., 2008). Current models of the BBB typically are two-dimensional (2D) co-culture models with cells plated on opposite sides of a porous polymer membrane or hollow cylinder. Generally, in vitro 2D models are based on a monolayer of BMECs plated on a porous membrane located between two chambers. Transendothelial resistance (TEER) measurements or permeability measurements are used to assess barrier properties. A wide range of configurations have been studied including: 2D monolayers of BMECs and astrocytes plated on opposite sides of the membrane support, BMECs and pericytes plated on opposite sides of a membrane support with astrocytes or astrocyte extract in one chamber, and variations where the BMECs are plated on membranes coated with ECM or basement membrane proteins (Hartmann et al., 2007; Cucullo et al., 2011; Nakagawa et al., 2009; Zozulya et al., 2008; Weidenfeller et al., 2007; Tilling et al., 1998; Rubin et al., 1991; Bickel, 2005; Ma et al., 2005; Siddharthan et al., 2007; Lundquist and Renftel, 2002; Lundquist et al., 2002).

The 2D models known in the art are not sufficiently close to capturing the physical and biological characteristics of the BBB to be widely used for BBB research. Key limitations of these models include no paracrine signaling between cells, astrocytes not in a physiologically relevant 3D matrix, and no shear flow.

Surprisingly little research aimed at developing an artificial capillary platform has been done, to date. Tien and coworkers have reported on an artificial vessel formed by seeding vascular endothelial cells on the internal surface of a cylindrical channel in a collagen matrix (Poller et al., 2008; Weksler et al., 2005; Hawkins et al, 2005; Wong et al., 2010). This vessel, however, is not a model for the BBB and does not include the relevant cell types.

The most advanced model of an artificial brain capillary has been developed by Janigro and co-workers and involves co-culture of endothelial cells and astrocytes onto impermeable, hollow cylinder polypropylene fibers (FIG. 1; Stanness et al., 1997; Cucullo et al., 2007). The polypropylene fibers have an inner diameter of 330 µm, a wall thickness of 150 µm, and 500-nm diameter pores in the wall. Bundles of these fibers are encased in cartridges with an external perfusion circuit, maintaining flow of culture medium with $CO_2$. Brain capillary endothelial cells and astrocytes are co-cultured on opposite sides of the fiber wall with human brain microvascular endothelial cells (hBMECs) on the luminal side and astrocytes on the outside. The relatively thick fiber walls with small cylindrical pores limit communication between hBMECs and astrocytes.

The hollow fiber scaffold approach for artificial brain capillaries has significant advantages over 2D planar membranes. The cylindrical geometry in the hollow fiber allows for axial flow and shear stresses that are physiologically relevant. The ability to co-culture brain capillary endothelial cells and astrocytes on these structures has resulted in in vitro models exhibiting many of the important characteristics of the BBB. While this co-culture model exhibits some of the important characteristics of the BBB and represents a major technical accomplishment, at least several aspects can be improved: (1) the limited porosity of the polymer membrane restricts access of nutrients to the basal surfaces of the cells; (2) the large wall thickness (150 µm) and small pore diameter (0.5 µm) of the hollow fiber membrane limits contact between the hBMECs and astrocytes and severely restricts paracrine signaling; (3) the polymer surfaces are not tailored for BMEC and astrocyte culture, lacking appropriate architecture and cell adhesion ligands; (4) the polymer tubes themselves are much larger in diameter (330 µm inner diameter) than typical brain microvasculature; (5) the vessel is not embedded in an extracellular matrix; and (6) the platform does not allow direct imaging.

SUMMARY

The presently disclosed subject matter provides an artificial BBB that can be used as a platform for developing therapies to treat diseases, disorders, and conditions that affect the central nervous system.

In some aspects, the presently disclosed subject matter provides an artificial blood-brain barrier (BBB) comprising a template comprising an inlet and outlet, wherein the template is operationally configured to contain a three-dimensional (3D) extracellular matrix (ECM) comprising at least one artificial vessel embedded therein, wherein the at least one embedded artificial vessel has an inner surface defined by at least a monolayer of endothelial cells, and wherein the at least one artificial vessel is in fluid communication with the inlet and outlet of the template.

In other aspects, the presently disclosed subject matter provides a method for fabricating an artificial blood-brain barrier (BBB) comprising a template comprising an inlet and outlet, wherein the template is operationally configured to contain a three-dimensional (3D) extracellular matrix (ECM) comprising at least one artificial vessel embedded therein, wherein the at least one embedded artificial vessel has an inner surface defined by at least a monolayer of endothelial cells, and wherein the at least one artificial vessel is in fluid communication with the inlet and outlet of the template, the method comprising: (a) providing a mold adapted to form the template, wherein the mold comprises one or more channels configured to define one or more walls of the template; (b) disposing a thermoplastic material into the mold and curing the thermoplastic material to form the template, wherein the template has an upstream end and a downstream end; (c) forming an inlet in the upstream end of the template and an outlet in the downstream end of the template; (d) inserting a rod extending from the inlet in the upstream end of the template to the outlet in the downstream end of the template; (e) disposing a material comprising the ECM into the template; (f) allowing the material comprising the ECM to gel, then removing the rod to form at least one embedded artificial vessel in the ECM; and (g) perfusing the at least one embedded artificial vessel in the ECM with endothelial cells to line an inner surface of the at least one embedded artificial vessel with at least a monolayer of endothelial cells.

In yet other aspects, the presently disclosed subject matter provides a method for modeling a disease, disorder, or condition in a subject, the method comprising: (a) obtaining cells from a subject having, suspected of having, or susceptible of having the disease, disorder, or condition; (b) disposing the cells into an artificial blood-brain barrier (BBB) comprising a template comprising an inlet and outlet, wherein the template is operationally configured to contain a three-dimensional (3D) extracellular matrix (ECM) comprising at least one artificial vessel embedded therein, wherein the at least one embedded artificial vessel has an inner surface defined by at least a monolayer of endothelial cells, and wherein the at least one artificial vessel is in fluid communication with the inlet and outlet of the template; and (c) determining an effect of the cells on the artificial BBB to model the disease, disorder, or condition in a subject. The disease, disorder, or condition can include, but is not limited to, a disease, disorder, or condition of the central nervous system, a cancer, thrombosis or stroke, angiogenesis, BBB disruption, or BBB repair.

BRIEF DESCRIPTION OF THE FIGURES

Figure 1:
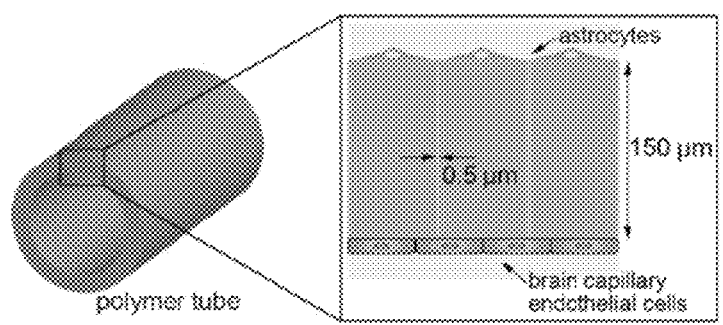
Figure 2:
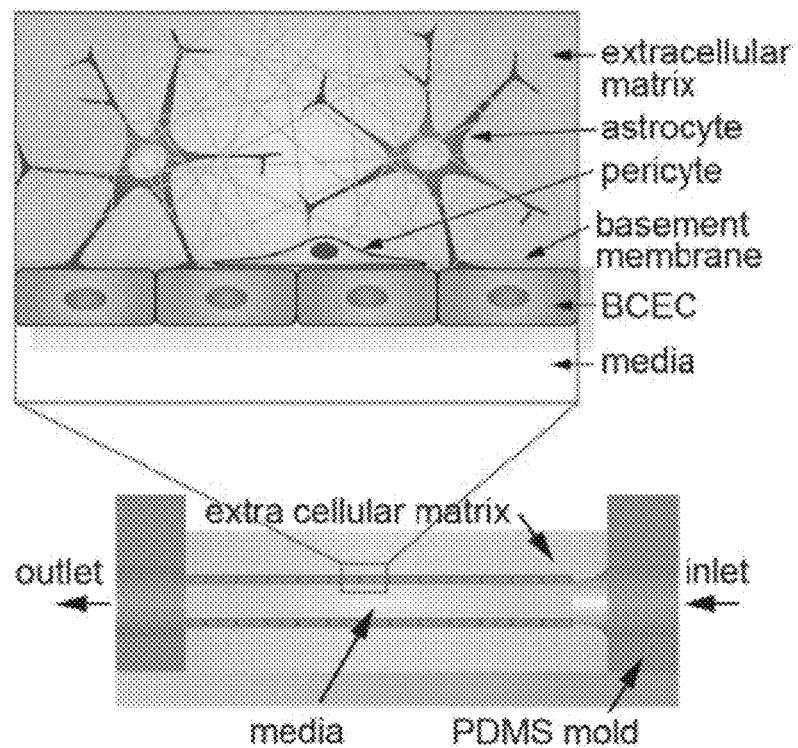

Having thus described the presently disclosed subject matter in general terms, reference will now be made to the accompanying Figures, which are not necessarily drawn to scale, and wherein:

FIG. 1 shows a current state-of-the-art BBB platform using a polymer tube about 300 µm in diameter as a template. The BMECs and astrocytes are plated on opposite sides of a 150-µm thick polymer with 0.5-µm pores to allow signaling. The illustration in the inset is approximately to scale (Prior Art);

FIG. 2 shows a schematic illustration of one embodiment of the presently disclosed artificial brain capillary platform. A cylindrical channel in the center of a hydrogel scaffold defines the capillary. Brain capillary endothelial cells are surrounded by pericytes, basement membrane, and astrocytes embedded in an ECM. The platform allows control of relevant physical, chemical, and biological parameters;

FIGS. 3a-3h show images of one embodiment of the stepwise fabrication of a presently disclosed ECM/vessel platform with three parallel vessels: (a) mold for platform. The rods provide the channels for connection to external tubing. Three central rectangular walls define the rectangular channels in which the ECM and artificial vessels are formed; (b) pouring polydimethylsiloxane (PDMS) into mold; (c) bonding PDMS template to glass slide. Holes for perfusion inlets and outlets punched into PDMS. Nozzles forming the interface between the PDMS and ECM are inserted into the channels; (d) cell injection ports and bubble traps for each channel added; (e) reservoirs for tumor cavities added; (f) hydrogel (ECM) introduced into the rectangular channels to form the vessels. Inlet and outlet ports for each channel added; (g) pressure relief valves added; and (h) platform on inverted microscope for imaging;

FIGS. 4a-4e show a schematic illustration of one embodiment of the formation of a presently disclosed artificial ECM/vessel in rectangular channels in the platform. (a) after insertion of the nozzles (see FIG. 4d above), a rod is inserted into the channel; (b) the material to be used for the artificial ECM is introduced into the rectangular cavity; (c) after gelation, the template rod is removed leaving a cylindrical channel in the hydrogel between the two nozzles; (d) the artificial vessel is formed after seeding with desired cells and perfusing; (e) further embodiments of the presently disclosed artificial BBB;

FIGS. 5a and 5b show the measurement of permeability coefficients: (a) fluorescently labeled dextran is injected into an artificial vessel for 2 min, followed by a 1-min stop and subsequent wash out. Scale bar is 100 µm; (b) intensities of fluorescent micrographs are plotted with respect to time, and permeability coefficients are calculated from the inset equation using extracted magnitudes and slopes from the graph; and FIGS. 6a-6d show a wide-field epifluorescence image of a presently disclosed artificial vessel with a confluent monolayer of D3 brain capillary endothelial cells surrounded by a collagen matrix: (a) phase contrast; (b) DAPI nuclear stain; (c) VE-cadherin junctional immunostain; and (d) F-actin phallotoxin stain.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The BBB is relevant to two critical, but related clinical problems: (1) the BBB is the major roadblock to treatment of CNS diseases; and (2) an urgent need to develop therapies to repair the BBB exists. The barrier function of the BBB is critical for maintaining homeostasis, but also represents a significant roadblock in delivering drugs to the brain (Ohtsuki and Terasaki, 2007; Pardridge, 2003; Pardridge, 2005; Pardridge, 2006; Pardridge, 2010; Pardridge, 2008). Only very few CNS disorders (depression, schizophrenia, chronic pain, and epilepsy) are currently treatable with small molecule drug therapy. Accordingly, the BBB is the major roadblock in developing therapies for CNS diseases including: neurodegenerative diseases, cerebrovascular diseases, and brain cancer.

Thus, a BBB platform would contribute to the development of new therapies for treating CNS diseases and hence have tremendous societal benefit through improved human health. The worldwide pharmaceutical market for CNS diseases was about $80 billion in 2010, approximately 20% of the total pharmaceutical market, despite the fact that about twice as many people suffer from CNS diseases compared to those that suffer from vascular diseases (thepharmaletter, 2010; Bourne-Partners, 2010). Furthermore, about 48% of the CNS market is the psychiatric sector, including antidepressants and antipsychotics. Treatments for Alzheimer's, Parkinson's, and MS are limited to disease modifying drugs that relieve symptoms but do not cure the disease. The rate-limiting step in drug discovery and the development of new therapies is a high-throughput model of the BBB.

Since the BBB is critical to maintain homeostasis in the brain, it is not surprising that disruption can lead to changes in permeability, modulation of immune cell transport, and trafficking of pathogens into the brain (Abbott et al., 2010; Neuwelt et al., 2011; Hawkins and Davis, 2005; Engelhardt, 2008; Engelhardt, 2008). Disruption of the BBB is associated with neurodegenerative diseases (Alzheimer's disease (Zlokovic, 2005; Kalaria, 1999; Zipser et al., 2007; Meyer et al., 2008; Hartz et al., 2010; Desai et al., 2007), ALS (Zhong et al., 2008), and Parkinson's disease (Desai et al., 2007; Bartels et al., 2008; Kortekaas et al, 2005), cerebrovascular diseases (e.g., stroke; Moskowitz et al., 2010; Belayev et al., 1996; Lo et al., 2003; Lippoldt et al., 2000; del Zoppo, 2010)), epilepsy and seizures (Remy and Beck, 2006; Oby and Janigro, 2006; Seiffert et al., 2004), brain infections (HIV encephalitis (Berger and Avison, 2004; Dallasta et al., 1999; Persidsky et al., 2006) and meningitis (Uchiyama et al., 2009), inflammatory diseases (MS; Minagar and Alexander, 2003; McQuaid et al., 2009; Gold et al., 2006; Waubant, 2006; Kermode et al., 1990) brain tumors (Bronger et al., 2005; Papadopoulos et al., 2004; Davies, 2002), and neurotrauma (Stahel et al., 2000; Kim and Dustin, 2006; Shlosberg et al., 2010).

The greatest risk factor for neurodegenerative disorders is aging and it has been hypothesized that aging of the vascular system, specifically the neurovascular unit containing the BBB, is the most important risk factor for neurodegeneration (Neuwelt, 2008). The association of BBB disruption with CNS diseases suggests that BBB repair may prove to be an effective approach to maintain health and aid recovery from disease, infection, or injury (Abbott et al., 2010).

The presently disclosed subject matter demonstrates a functional, perfused artificial vessel or capillary, lined with brain capillary endothelial cells and embedded in a 3D extracellular matrix. Herein is disclosed a device to create such an artificial BBB, methods of creating the artificial BBB, the artificial BBB itself, and methods for use of the artificial BBB.

I. DEVICE AND METHODS TO CREATE A 3D ARTIFICIAL BLOOD-BRAIN BARRIER

The presently disclosed subject matter provides a platform to create a three dimensional (3D) artificial BBB that preserves the relevant in vivo physiological geometry in an in vitro setup. The device creates one or more artificial capillaries lined with cells, such as brain microvascular endothelial cells (BMEC) embedded in a 3D extracellular matrix (ECM) in a template. In some embodiments, the template is a transparent thermoplastic template. The ECM may additionally be cultured with other types of cells such as astrocytes and pericytes.

The presently disclosed subject matter addresses key problems associated with making connections to the ends of the capillary or vessel, embedding the vessel in a physiologically relevant extracellular matrix, and forming a confluent monolayer of endothelial cells in the vessel. By engineering a physiological ECM (geometry, composition, cross-linking, and the like) and co-culturing endothelial cells with astrocytes and pericytes, the brain microenvironment can be mimicked and the properties of a functional BBB recapitulated.

In some embodiments, the presently disclosed subject matter provides a "bottom up" approach to building a physiologically relevant BBB microenvironment. This approach allows incorporation of the different cell types (BMECs, astrocytes, pericytes, and the like) in a physiologically relevant geometry. The BBB is a dynamic interface that transduces signals from the vascular system and the central nervous system. To capture the important physical and biological characteristics of the BBB, the local microenvironment should be fully recapitulated on both sides of the interface. Accordingly, to create an in vitro model that will facilitate BBB research, an artificial brain capillary embedded in extracellular matrix is fabricated.

One feature of the presently disclosed approach is to form the capillary in a cylindrical channel in a 3D matrix that provides a physiologically relevant microenvironment (FIG. 2). Therefore, the matrix serves as an artificial extracellular matrix, allowing a range of biochemical and micromechanical signaling and transport processes.

The presently disclosed artificial ECM/capillary platform allows study of the BBB in a physiologically relevant geometry. The platform allows the degree of complexity to be increased systematically, and biological and physicochemical variables to be controlled independently. These variables include, but are not limited to, physical and mechanical properties of the ECM (e.g., fiber size, cross-linking, pore size, stiffness, and the like), chemical properties of the ECM (composition, e.g., collagen, hyaluronic acid, composite gel, and the like), biological properties of the ECM (e.g., growth factors, cytokines, signaling molecules, and the like), cell types (e.g., BMECs, astrocytes, pericytes, and the like), physico-chemical properties of the vessel (vessel diameter, shear stress/flow rate, pressure, viscosity, and the like), and concentration of signaling molecules, drugs, and other cell types in the vessel.

In some embodiments, the presently disclosed subject matter provides a device that allows for the manufacture of a 3D artificial BBB by creating a hollow tube in an artificial 3D extracellular matrix (ECM) in a transparent thermoplastic template, the device comprising a container, wherein the container is a mold for forming a transparent thermoplastic microfluidic template and the at least one microchannel is a mold for forming an artificial 3D ECM, and wherein the at least one microchannel has a diameter having a range from about 25 μm to about 250 μm. The interior of the tube is lined with cells to mimic the inside of a capillary and the ECM is cultured with relevant cells to mimic the brain side of the barrier. This approach allows the cells to assume natural, 3D, physiologically relevant geometries in a transparent setting.

The material that comprises the mold for the device can be a metal, such as aluminum, stainless steel, and the like, a plastic, glass, a composite, or any material that can hold its shape and act as a mold.

Generally, in some embodiments, the presently disclosed subject matter provides a method for fabricating an artificial blood-brain barrier (BBB) comprising a template comprising an inlet and outlet, wherein the template is operationally configured to contain a three-dimensional (3D) extracellular matrix (ECM) comprising at least one artificial vessel embedded therein, wherein the at least one embedded artificial vessel has an inner surface defined by at least a monolayer of endothelial cells, and wherein the at least one artificial vessel is in fluid communication with the inlet and outlet of the template, the method comprising: (a) providing a mold, see, e.g, mold 300 in FIG. 3a, adapted to form the template, wherein the mold comprises one or more channels, see, e.g., elements 310 in FIG. 3b, configured to define one or more walls of the template; (b) disposing a thermoplastic material into the mold and curing the thermoplastic material to form the template, wherein the template has an upstream end and a downstream end; (c) forming an inlet in the upstream end of the template for an inlet port and an outlet in the downstream end of the template for an outlet port; (d) inserting a rod extending from the inlet in the upstream end of the template to the outlet in the downstream end of the template, wherein the rod is aligned with the inlet and outlet ports; (e) disposing a material comprising the ECM into the template; (f) allowing the material comprising the ECM to gel, then removing the rod to form at least one embedded artificial vessel in the ECM; and (g) perfusing the at least one embedded artificial vessel in the ECM with endothelial cells to line an inner surface of the at least one embedded artificial vessel with at least a monolayer of endothelial cells.

More particularly, referring now to FIG. 3a-3h, the presently disclosed subject matter provides methods for creating a 3D transparent microfluidic BBB comprising one or more artificial capillaries embedded in an artificial 3D extracellular matrix. In some embodiments, the method comprises: (a) pouring a transparent thermoplastic into the container of the device disclosed herein, the device comprising a container, at least one microchannel within the container, and a rod attached to each side of the at least one microchannel that provides a channel for connection to external tubing; wherein the container is a mold for forming a transparent thermoplastic microfluidic template and the at least one microchannel is a mold for forming an artificial 3D ECM; and wherein the at least one microchannel has a diameter having a range from about 25 µm to about 250 µm; (b) allowing the transparent thermoplastic to harden to form a transparent thermoplastic template; (c) removing the thermoplastic template from the device disclosed herein, and laying the thermoplastic template on a flat surface; (d) removing a portion of the thermoplastic template to allow access to the at least one microchannel and adding a nozzle at each side into the at least one microchannel; (e) inserting a removable rod into each nozzle within the at least one microchannel; (f) adding a hydrogel or hydrogel composite into the at least one microchannel to form an artificial 3D ECM; (g) allowing the hydrogel or hydrogel composite to harden; and (h) removing the removable rod to form a microvessel or artificial capillary.

In some embodiments, the thermoplastic material is selected from the group consisting of polydimethylsiloxane (PDMS) and poly(methyl methacrylate) (PMMA). In other embodiments, the method further comprises oxidizing the thermoplastic material before it is poured into the device. In still other embodiments, the method comprises oxidizing the template with plasma oxidation. In further embodiments, the method further comprises gelling the material comprising the ECM in the presence of ammonia vapor.

In some embodiments, the inlet and the outlet further comprise a nozzle. It has been found that it can be advantageous for the nozzle to be on the upstream or the input side of the microchannel and extend into the opening of the microchannel. Therefore, in some embodiments, the nozzle on the upstream side of the microchannel extends into the opening of the microchannel.

Once the nozzles are attached to the microchannel, a removable rod is inserted into the nozzles. In some embodiments, the removable rod is cylindrical. In other embodiments, the methods further comprise modifying one or more external surfaces of the rod with a surfactant prior to inserting the rod to extend from the inlet in the upstream end of the template to the outlet in the downstream end of the template. In further embodiments, the removable rod is immersed in a nonionic surfactant prior to being inserted into the nozzle. In further embodiments, the nonionic surfactant is Pluronic® F-127, or an equivalent nonionic surfactant.

Once the removable rod is inside the microchannel, an artificial ECM material is added to the microchannel from a hole that is formed when a portion of the thermoplastic template is removed. In some embodiments, the artificial ECM material comprises a hydrogel or hydrogel composite, including, but not limited to, collagen, matrigel, laminin, fibrin, and hyaluronic acid (HA), and combinations thereof. In other embodiments, the hydrogel or hydrogel composite exhibits a continuously porous or fibrous structure.

In some embodiments, the method further comprises cross-linking the material comprising the ECM. In particular embodiments, the cross-linking includes the formation of covalent amide bonds. In further embodiments, the covalent amide bonds are formed via the addition of bis[sulfosuccinimidyl] suberate. In further embodiments, cross-linking results in ECM channels having diameters exhibiting less than about 10% elastic expansion when exposed to intraluminal pressures greater than about 50 cm of water. The ECM can be returned to physiological conditions by perfusing buffer solutions comprising components that have characteristics of physiological conditions.

The ECM provides mechanical support for endothelial cells faced with intraluminal pressure fluctuations and shear stress. By tuning ECM composition, concentration, and cross-linking, properties important for biochemical and mechanical signaling between co-cultured cell types (pericytes, astrocytes, endothelial cells) can be modulated.

In some embodiments, the method further comprises modifying one or more of internal surfaces of the template with a silane/epoxy to prevent delamination. In further embodiments, the silane/epoxy comprises (3-glycidyloxypropyl) trimethoxysilane.

In other embodiments, cells are introduced into the microvessel through perfusion. In some embodiments, the cells added to the microvessel are endothelial cells. In further embodiments, a confluent monolayer of endothelial cells is formed in the artificial capillary or microvessel. The endothelial cells may comprise vascular endothelial cells, such as brain microvascular endothelial cells. In other embodiments, the endothelial cells are human cells.

In some embodiments, the ECM further comprises at least one component selected from the group consisting of an astrocyte, a pericyte, a signaling molecule, fibrin, elastin, a proteoglycan, nonfibrillar collagen, and a basement membrane protein to further mimic the in vivo conditions of the BBB. In other embodiments, the ECM further comprises at least one component selected from the group consisting of fibrin, elastin, a proteoglycan, and a nonfibrillar collagen. In further embodiments, the ECM further comprises at least one or more of an astrocyte, a pericyte, and a basement membrane protein. These other components may be added to the ECM before, during, or after the ECM material has hardened in the thermoplastic template.

To allow the movement of liquid through the system, at least one hole for a perfusion inlet or outlet is created in the thermoplastic template. In other embodiments, at least one cell injection port or bubble trap is added to the thermoplastic template. In still other embodiments, at least one reservoir is added to the thermoplastic template. In further embodiments, at least one inlet or outlet port is added to the thermoplastic template. In still further embodiments, at least one pressure relief valve is added to the thermoplastic template. Accordingly, in some embodiments, the method further comprises operationally connecting at least one component selected from the group consisting of a bubble trap, a reservoir, a pressure relief valve, and combinations thereof, to the at least one artificial vessel.

At least one advantage of these methods is that, in some embodiments, the artificial BBB can be visualized through light microscopy. In other embodiments, a cell can be visualized in real time.

In some embodiments, it has been found that the artificial microvessels of the BBB are stable at shear stresses up to about 10 dynes cm$^{-2}$. In other embodiments, it has been found that the microvessels are stable at shear stresses up to about 30 dynes cm$^{-2}$ with the addition of dextran to the buffer. In further embodiments, the permeability coefficient of the microvessel is about $7 \times 10^{-6}$ cm s$^{-1}$ or lower.

Using the presently disclosed methods, the fabrication yield has been found to be more than 50%. The fabrication yield refers to the percentage of artificial BBBs that are viable and useable after being prepared in a mold.

II. THE ARTIFICIAL BLOOD-BRAIN BARRIER

The presently disclosed subject matter provides a 3D artificial microfluidic BBB that is transparent. The artificial BBB is a functional, perfused artificial vessel or capillary embedded in a 3D extracellular matrix in a transparent thermoplastic template. The artificial capillary can be lined with cells, such as brain microvascular endothelial cells, to mimic an actual BBB.

The system provides the most biologically relevant in vitro alternative to studying the BBB by allowing cells to migrate through the ECM and assume their natural orientation. The system is visually accessible and optically transparent through light microscopy, allowing for real time, live cell microscopy.

In addition, the system can function as a microfluidic device, controlling perfusion of the vessel and providing bubble traps and pressure release valves, and cell injection ports. Because the presently disclosed device can function as a microfluidic device with external nozzles, flow rate, and hence shear stress, the capillary can be modified and studied.

Accordingly, the presently disclosed subject matter provides an artificial blood-brain barrier (BBB) comprising a template comprising an inlet and outlet, wherein the template is operationally configured to contain a three-dimensional (3D) extracellular matrix (ECM) comprising at least one artificial vessel embedded therein, wherein the at least one embedded artificial vessel has an inner surface defined by at least a monolayer of endothelial cells, and wherein the at least one artificial vessel is in fluid communication with the inlet and outlet of the template.

As described herein, the artificial BBB comprises a thermoplastic material. In some embodiments, the thermoplastic material comprises an optically transparent thermoplastic material. In some embodiments, the thermoplastic template is modified at the surfaces with a silane or epoxy.

The thermoplastic template is removed from the device and placed on a flat surface. In some embodiments the thermoplastic template is bonded to glass, such as a glass plate or slide. In other embodiments, at least one hole for a perfusion inlet or outlet is created in the thermoplastic template.

In still other embodiments, the inlet and the outlet further comprise a nozzle. In further embodiments, the nozzle on the upstream side of the one or more microchannels extends into the opening of the ECM. In still further embodiments, a template further comprises at least one component selected from the group consisting of a bubble trap, a reservoir, a pressure relief valve, and combinations thereof, each of which, if present, are in fluid communication with the at least one artificial vessel.

The artificial ECM comprises a polymer scaffold that mimics the extracellular matrix found in vivo and exhibits a continuously porous/fibrous structure. In some embodiments, the ECM comprises a hydrogel or a hydrogel composite. In other embodiments, the hydrogel or hydrogel composite is selected from the group consisting of collagen, matrigel, laminin, fibrin, and hyaluronic acid.

In some embodiments, the ECM is modified through cross-linking. For example, in some embodiments, the cross-linking occurs by the addition of covalent amide bonds. In other embodiments, the covalent amide bonds are formed through the use of bis[sulfosuccinimidyl] suberate.

Various cell types can be cultured in the system, such as BMECs, astrocytes, and pericytes. The artificial ECM can be tailored for relevant cells to co-culture and allows the cultured cell types, such as endothelial cells, astrocytes, and pericytes, to migrate and remodel their surroundings to better conform and mimic the BBB. In addition, proteins, such as basement membrane proteins, can be added to further mimic the BBB.

In some embodiments, the microvessel is lined with endothelial cells. In other embodiments, the endothelial cells form a confluent monolayer. In further embodiments, the endothelial cells are brain microvascular endothelial cells. In still further embodiments, the endothelial cells are human cells. In other embodiments, the microvessel has a diameter having a range from about 10 µm to about 250 µm.

Each thermoplastic template can comprise one, two, three or more microvessels. In some embodiments, three microvessels are formed in each thermoplastic template.

In some embodiments, each microvessel is stable at shear stresses up to about 30 dynes cm$^{-2}$, shear stresses typically encountered in brain microvessels.

The artificial BBB is optically transparent and therefore the cells and the ECM in the BBB are easy to visualize. In other embodiments, the cells in the BBB are visualized in real time. Accordingly, in some embodiments, the artificial BBB further comprises an optical microscope operationally configured to view in real time one or more live cells comprising the artificial BBB.

III. METHODS USING THE ARTIFICIAL BLOOD-BRAIN BARRIER

The BBB is a dynamic interface responsible for maintaining homeostasis of the brain. The details and structure of it are not fully understood. A physiologically relevant in vitro model of the BBB allows a better understanding of the BBB. In addition, an artificial BBB allows for treatment of diseases of the central nervous system by allowing for rapid evaluation of pharmaceutical activity across the BBB in addition to providing a means to test treatments for diseases as opposed to symptom relief.

In some embodiments, the presently disclosed subject matter provides a method for modeling a disease, disorder, or condition in a subject, the method comprising: (a) obtaining cells from a subject having, suspected of having, or susceptible of having the disease, disorder, or condition; (b) disposing the cells into an artificial blood-brain barrier (BBB) comprising a template comprising an inlet and outlet, wherein the template is operationally configured to contain a three-dimensional (3D) extracellular matrix (ECM) comprising at least one artificial vessel embedded therein, wherein the at least one embedded artificial vessel has an inner surface defined by at least a monolayer of endothelial cells, and wherein the at least one artificial vessel is in fluid communication with the inlet and outlet of the template; and (c) determining an effect of the cells on the artificial BBB to model the disease, disorder, or condition in a subject.

In further embodiments, the cells are selected from the group consisting of brain endothelial cells, astrocytes, and pericytes. In other embodiments, the disease, disorder, or condition comprises a disease, disorder, or condition of the central nervous system. In other embodiments, the disease, disorder, or condition of the central nervous system is selected from the group consisting of Alzheimer's disease, Amyotrophic Lateral Sclerosis (ALS or Lou Gehrig's disease), Parkinson's disease, Dementia with Lewy Bodies, Huntington's disease, stroke, epilepsy, seizures, autism, brain infections, HIV, HIV encephalitis, neuro-AIDS, meningitis, inflammatory diseases, Multiple Sclerosis (MS), brain tumors, neurotrauma, depression, psychosis, schizophrenia, chronic pain, trauma, exposure to electromagnetic radiation, drowsiness, and neurodegeneration caused by aging.

In still further embodiments, a drug or combination of drugs is added to the artificial BBB before, during, or after the addition of cells from a patient with the disease, disorder, or condition to determine the effect of the drug or combination of drugs on the disease, disorder, or condition. The drug or combination of drugs can be added to the artificial BBB by perfusion. In some embodiments, at least one of the drugs is a small molecule drug. In other embodiments, at least one of the drugs is a peptide. In some embodiments, nanoparticles may be used for drug delivery to the BBB. In other embodiments, liposomes may be loaded with a drug or combination of drugs and added to the BBB.

The methods can also be used for modeling thrombosis or stroke in an artificial BBB. In some embodiments, the disease, disorder, or condition comprises thrombosis or stroke. The method further comprises adding a micro-bubble or a clotting agent to the artificial BBB. In some embodiments, a drug or combination of drugs is added to the BBB before, during, or after the injection of the micro-bubble or clotting agent to determine the effect of the drug or combination of drugs. Examples of clotting agents include, but are not limited to, vitamin K, fibrinogen, blood coagulation factors, aminocaproic acid, and tranexamic acid. In other embodiments, a potential clotting agent is added to an artificial BBB to test the agent for clotting characteristics.

Methods for modeling BBB disruption also are disclosed herein. In some embodiments, the method further comprises adding a drug or therapeutic agent or a combination of drugs or therapeutic agents or other external condition that is expected to cause BBB disruption to the artificial blood-brain barrier (BBB) and determining if the drug or therapeutic agent or other external condition causes disruption to the artificial BBB. In further embodiments, the external condition comprises electromagnetic radiation. In still further embodiments, disruption includes a change in at least one of the following conditions selected from the group consisting of permeability, immune cell transport, and trafficking of pathogens into the brain.

In some embodiments, the disease, disorder, or condition comprises blood-brain barrier (BBB) repair. In still other embodiments, the disease or trauma is added by adding cells to the artificial BBB from a subject that has undergone the disease or trauma.

IV. DEFINITIONS

As used herein, the terms "artificial blood-brain barrier," "artificial BBB," or "artificial capillary platform" refers to a model of an in vivo blood-brain barrier.

As used herein, the terms "brain microvascular endothelial cell" or "BMEC" and "brain capillary endothelial cell" or "BCEC" are used interchangeably.

As used herein, a "mold" refers to a container used to give shape to a liquid material, such that when the material hardens, solidifies, or gels, the liquid takes on the shape of the mold.

As used herein, an "artificial capillary" or an "artificial vessel" refers to a cylindrical channel embedded within the extracellular matrix, wherein the channel has an inner surface defined by at least a monolayer of endothelial cells.

As used herein, the "extracellular matrix" or "ECM" refers to the matrix present in which the artificial capillary or vessel is located. Basement membrane proteins and/or other types of proteins or molecules can be added to the ECM to form an additional part of the ECM.

"Basement membrane proteins" refer to proteins that form the basement membranes of the ECM.

As used herein, a "channel" refer to a passage through which liquids can pass.

As used herein, "embedded" refer to an object that is fixed firmly in a surrounding mass.

As used herein, "optically transparent" refer to a material through which light, e.g., light of visible wavelengths, can pass. In some embodiments, the material may be optically transparent to the naked eye. For example, the optically transparent material may be placed on a microscope, allowing light to pass through the material and allowing visualization of cells on or in the optically transparent material.

As used herein, "porous" is meant to refer a structure that has minute holes through which liquid or air can pass.

As used herein, "fiber" or "fibrous" is meant to refer to a slender, elongated, threadlike structure. In some embodiments, "fibrous" refers to the filaments comprising the ECM.

"Continuous porous and fibrous structure", means that the structure is mostly porous and fibrous. For example, more than 50% of the structure may be porous and fibrous, such as 55%, 65%, 75%, 85%, or more than 95%.

The "physiological properties of a natural blood-brain barrier" refers to those properties that are found in a BBB in vivo. Such properties include, but are not limited to, the components of a natural BBB, the spatial arrangements of the components, the ability of specific compounds to diffuse or be actively transported across the BBB (permeability), immune cell transport, trafficking of pathogens, and the like.

As used herein, "cross-linked" means that adjacent chains of a polymer or protein are joined by creating covalent bonds.

"Fibrin" refers to a fibrous, non-globular protein involved in the clotting of blood.

"Elastin" refers to a protein in connective tissue that is elastic and allows many tissues to resume their shape after stretching or contracting.

A "proteoglycan" refers to a protein that is heavily glycosylated and occurs in the extracellular matrix of connective tissue.

"Collagen" refers to a group of proteins that are the main component of connective tissue.

As used herein, a "fibril" refers to a small, slender fiber or part of a fiber. Therefore, "nonfibrillar collagen" refers to collagen that does not have a significant amount of small, slender fibers.

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. It will be appreciated that, although not precluded, treating a disease, disorder or condition does not require that the disease, disorder, condition or symptoms associated therewith be completely eliminated.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for treating an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In addition, the artificial BBB of the presently disclosed subject matter may comprise cells from any vertebrate species, such as those listed above.

Unless defined otherwise, all technical and scientific terms used herein have the meaning commonly understood by a person skilled in the art to which this invention belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Platform Fabrication

The presently disclosed microfluidic platform relies on a hydrogel (e.g., collagen, matrigel, hyaluronic acid, and the like) or a hydrogel composite (e.g., collagen, laminin, fibrin, hyaluronic acid, and the like) as an artificial ECM and vascular endothelial cells to define the vessel. The steps involved in fabricating one embodiment of the platform are shown in FIG. 3.

Figure 3:
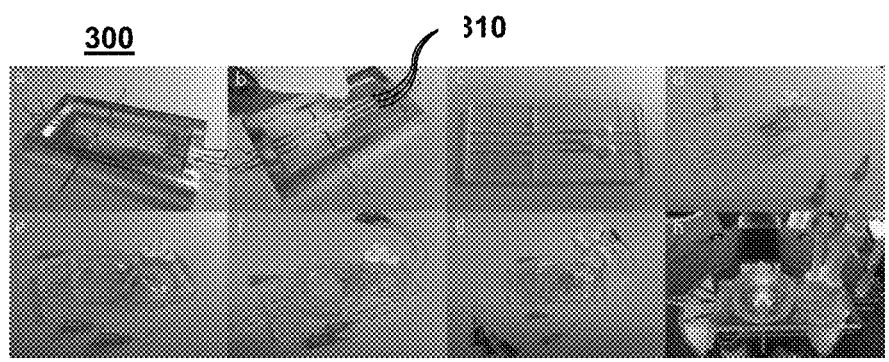

Referring now to FIG. 3, the central component of the platform is the polydimethylsiloxane (PDMS) microfluidic template formed by pouring PDMS into a custom designed aluminum mold 300 (FIGS. 3a-c). The device for preparing the artificial BBB is shown in FIG. 3a. Three central rectangular walls define the rectangular channels 310 in which the artificial ECM and artificial vessels are formed. In this embodiment, stainless steel dowels form interconnections between the device and tubing (FIG. 3b). The PDMS is poured into the device and allowed to harden to form the PDMS template, which provides the rectangular channels that are used as a mold for the ECM that will define the vessels. In the embodiment shown, the channels are 1.4 mm×1.4 mm in cross-section and 25 mm in length. The PDMS template can then be bonded to a glass slide as shown in FIG. 3c. Holes for perfusion inlets and outlets are punched into the PDMS. Nozzles forming the interface between the PDMS and ECM are inserted into the channels to funnel the flow and define ECM boundaries. In the embodiment of the platform shown, three vessels are formed in each template (FIG. 3d). Cell injection ports and bubble traps for each channel are added. FIG. 3e shows the addition of reservoirs, for tumor cavities, for example. The hydrogel (ECM) is introduced into the rectangular channels to form the vessels (FIG. 3f). Inlet and outlet ports for each channel are added. In addition, reservoirs can be added. FIG. 3g shows the addition of pressure relief valves. FIG. 3h shows the device on an inverted microscope for imaging.

The thermoplastic template can function as a microfluidic device, controlling perfusion of the vessel and providing bubble traps and pressure release valves, and cell injection ports.

Figure 4:
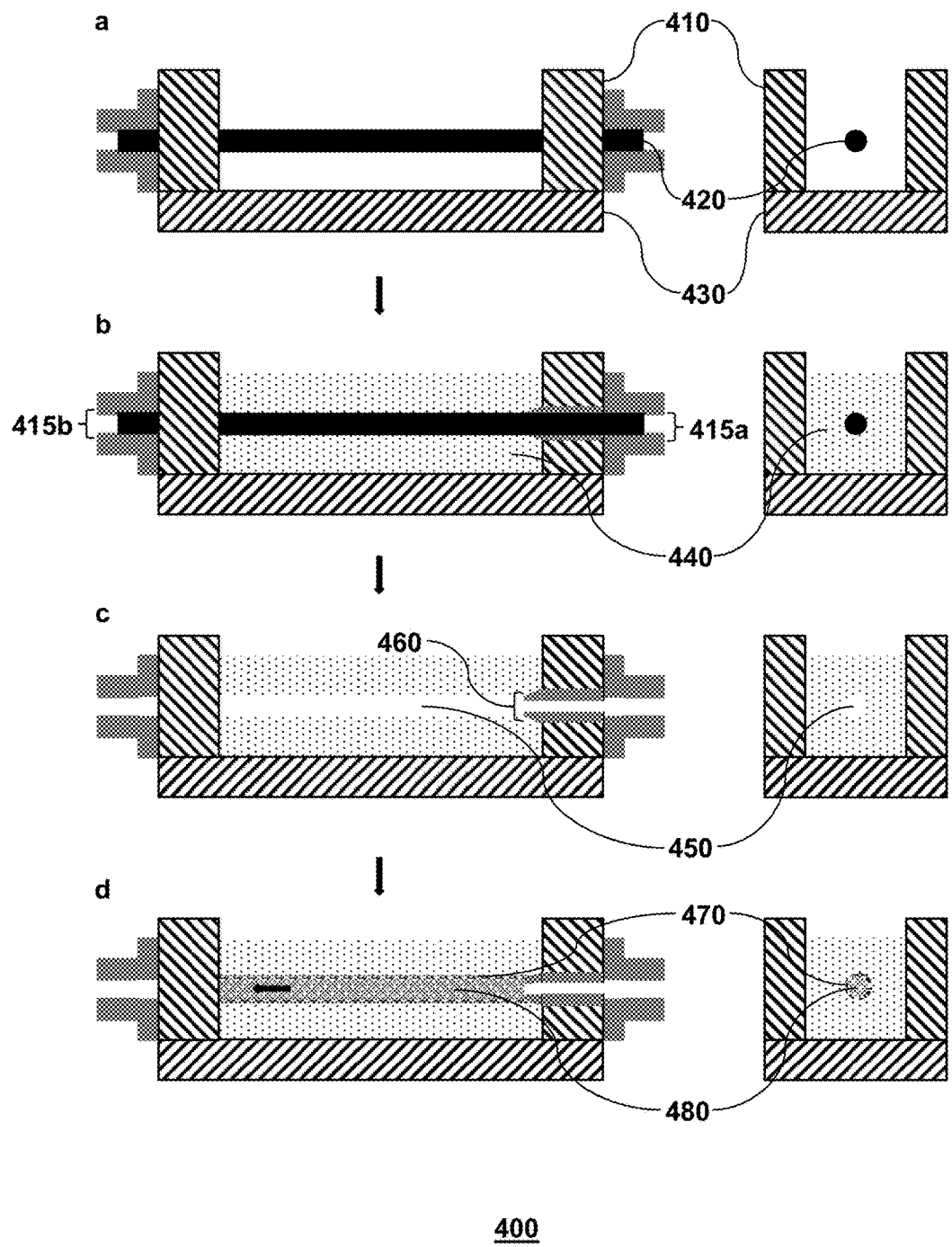

The details of formation of the ECM and vessel in the matrix are illustrated schematically in one embodiment in FIG. 4. Nozzles are inserted into the cylindrical holes in the PDMS at each end of the rectangular opening in the template (FIG. 4a). The nozzle on the upstream side extends into the opening and is important for successful device function. A cylindrical rod is then threaded between the two nozzles. This rod serves as the template for the cylindrical channel that will form the vessel or artificial capillary. The ECM material (e.g., collagen) is poured into the rectangular opening in the PDMS (FIG. 4b). After gelation of the ECM, the rod is removed leaving a cylindrical channel (FIG. 4c). The rod is immersed in Pluronic® F-127 for at least 4 hours and air-dried prior to inserting into the nozzles. This pre-treatment prevents adhesion of the ECM material and ensures smooth removal without the formation of defects such as rips or tears in the collagen. The channel is then perfused and endothelial cells plated in the channel to form the lumen of the vessel (FIG. 4d).

Referring once again to FIG. 4, provided therein is platform 400 for forming an artificial BBB. Platform 400 comprises template 410, which in some embodiments, comprises a transparent thermoplastic material, such as PDMS. Platform 400 further comprises rod 420, which extends from inlet 415a in an upstream end of template 410 to outlet 415b in a downstream end of template 410. The horizontal arrow in FIG. 4d indicates the direction of flow. In some embodiments, template 410 is bonded to glass surface 430. Platform 400 further comprises three-dimensional extracellular matrix (ECM) 440, which surrounds rod 420. Once rod 420 is removed, ECM 440 comprises artificial vessel 450, which is in fluid communication with nozzle 460 and has an inner surface defined by at least a monolayer of endothelial cells 470. Artificial vessel 450 can be perfused or injected with fluid 480.

Figure 4E:
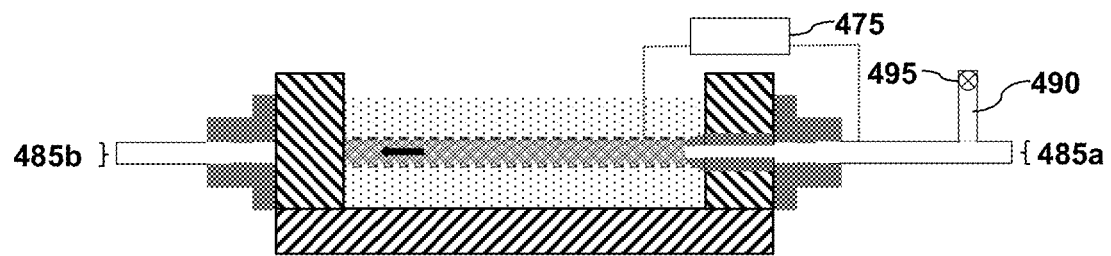

Referring now to FIG. 4e, in some embodiments, also included in the platform 400 is cell injection port 485a, which is in fluid communication with inlet 415a and exit port 485b, which is in fluid communication with outlet 415b.

In further embodiments, platform 400 also includes bubble trap 490, which, in some embodiments, can be in fluid communication with cell injection port 485. Also, in further embodiments, bubble trap 490 can include pressure relief valve 495. Further, in additional embodiments, platform 400 can include cell reservoir 475, which can be in fluid communication with cell injection port 485 and/or artificial vessel 450. One of ordinary skill in the art would recognize that the components of platform 400 can be configured in other arrangements suitable for use with the presently disclosed subject matter.

In designing the device and methods of the presently disclosed subject matter, three particularly challenging engineering problems were encountered: (1) delamination along the PDMS/collagen interface due to poor adhesion; (2) delamination at the entrance and exit points; and (3) bursting of the ECM under pressure due to heterogeneous gelation. The first problem was addressed by introduction of the nozzles, with the upstream nozzle extending into the opening. The second problem was addressed by plasma oxidation of the PDMS template followed by surface modification of the internal surfaces with a silane/epoxy. The third problem was addressed by using ammonia vapor (rather than NaOH solution) for gelation. By designing the platform so that the rectangular channels in the PDMS can be accessed from above, gelation is sufficiently uniform to eliminate the problem of failure under pressure. Having addressed these engineering problems, the fabrication yield is very high (>50%).

Example 2

Extracellular Matrix (ECM)

The ECM scaffold is formed by pouring a solution of collagen type I (BD Sciences) in acetic acid 0.02N into the PDMS device (FIGS. 3f and 4b). As disclosed hereinabove, the PDMS and glass surfaces are first modified with (3-glycidyloxypropyl) trimethoxysilane. The collagen solution is allowed to bind to the activated surfaces of the template for about 30 minutes and then gelled at room-temperature using ammonium hydroxide vapors to increase the solution pH. This approach results in uniform gelation of the collagen with high optical transparency. After gelation, the template rod is removed, leaving behind a cylindrical channel with an inner diameter no more than 5% greater than that of the original template (FIG. 4c). Through an open face above the gel, a cell-impermeable BS3 cross linker (bis[sulfosuccinimidyl] suberate; BSSS) is introduced, which has sulfo-NHS esters located at both ends of an 11.4 Å spacer arm to cross-link the collagen matrix with covalent amide bonds. At higher collagen matrix concentrations, this cross-linking results in robust collagen channels with diameters showing less than 10% elastic expansion when exposed to intraluminal pressures greater than 50 cm of water. After neutralizing the cross-linker, the gel is perfused with PBS at pH 7.4 to return the matrix to physiological conditions suitable for introducing endothelial cells. To optimize for astrocyte morphology, the ECM can be modified by incorporating fibrin, elastin, proteoglycans (e.g., hyaluronic acid, alginate), and nonfibrillar collagen as well as other adhesion molecules (Griffith and Swartz, 2006).

Example 3

Perfusion and Shear Stress

The normal time-averaged levels of shear stress in the venous and arterial circulation vary between 1 dynes cm$^{-2}$ to 4 dynes cm$^{-2}$ and 4 dynes cm$^{-2}$ to 30 dynes cm$^{-2}$, respectively (Turitto, 1982). For Poiseuille flow in a circular vessel, the shear stress t is given by $\tau=4\mu Q/(\pi r^3)$ where $\mu$ is the dynamic viscosity, Q is the volumetric flow rate, and r is the radius of the lumen. The viscosity of blood is about 4 cP, significantly larger than the viscosity of water (0.7 cP at 37° C.) primarily due to the presence of red blood cells. To achieve a shear stress of 10 dynes cm$^{-2}$ (1 Pa) in a 150 μm vessel in buffer, requires a flow rate of about 28 μL min$^{-1}$ in buffer or 5 μL min$^{-1}$ in blood. Perfusion is achieved through a syringe pump or gravity flow. The presently disclosed artificial vessels are stable at these flow rates. To achieve the full range of physiological shear stress, the media viscosity can be increased by using dextran. A viscosity of about 4 cP can be achieved with around 2% of 100 kDa dextran (Armstrong et al., 2004). Dextran solutions are used for blood transfusions in emergency situations and hence are physiologically relevant.

Example 4

Cell Lines

Protocols have been developed herein for introducing and incubating endothelial cells to form the lumen of the artificial vessel. Examples of cell types that can be used include primary human microvascular endothelial cells and D3 human brain capillary endothelial cells. Additional cell lines can also be used, such as primary rat BMECs.

Cell lines from diseased subjects can be added to the artificial BBB of the presently disclosed subject matter to study the disruption or change of the BBB as a result of the cells from a diseased subject. For example, primary human brain endothelial cells can be collected from epileptic patients to explore the disruption of the BBB in epilepsy and the efficacy of possible therapies.

Example 5

Vessel Characterization

The requirements for an in vitro BBB model include endothelial cell morphology typical of a quiescent vessel, restricted paracellular transport, and expression of specific markers (Hawkins and Davis, 2005). Optimized platforms can be assessed by measuring endothelial cell morphology and dynamics (cell morphology, cell turnover, cell motility), barrier function (permeability measurements), and protein expression (e.g., junction proteins, transporters, and the like).

Example 6

Endothelial Cell Morphology and Dynamics

Cell morphology can be quantitatively characterized from analysis of confocal microscopy images after staining for junction proteins such as Claudin-5 or ZO-1.

For quantitative analysis of cell morphology, a method has been developed for unwrapping confocal microscope images of vessels and digitizing the network of cell-cell junctions. From the digitized images, the cell morphology (area, shape factor, aspect ratio, long axis orientation) can be quantitatively characterized. The mitotic index (percent of cells dividing in 24 hours) can be determined by imaging portions of the vessel every 20 minutes.

Example 7

Barrier Function

Figure 5:
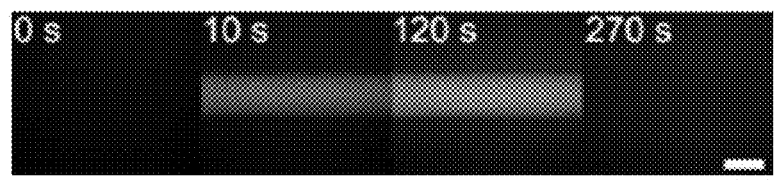
Figure 5:
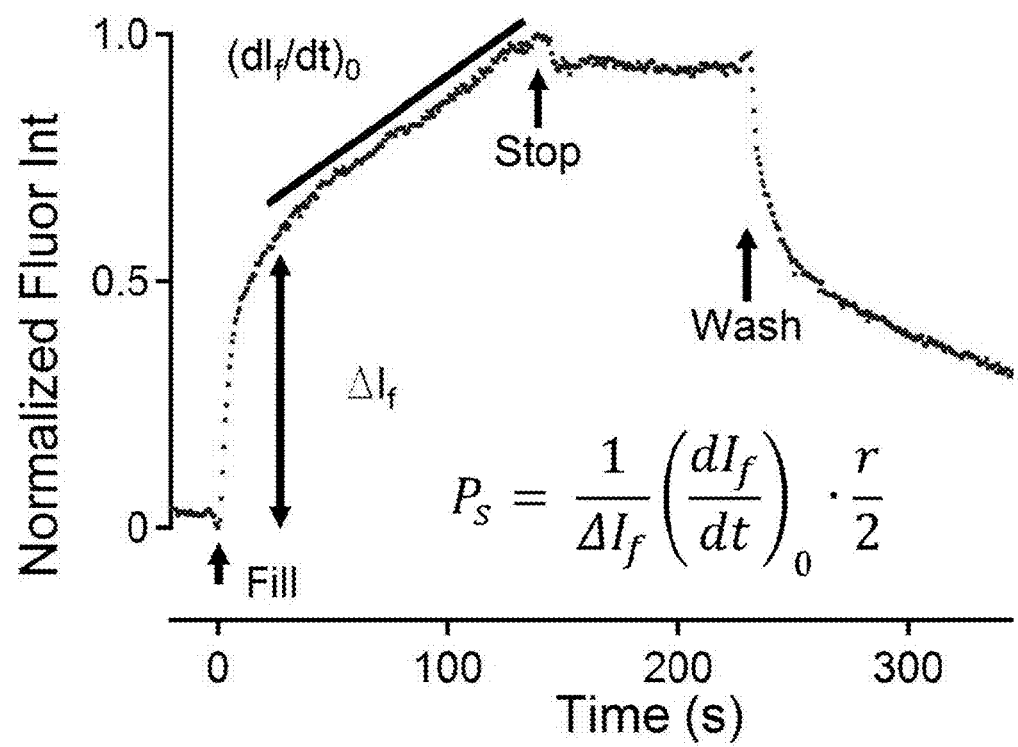

Permeability coefficients of the vessels (Chrobak et al., 2006; Yuan et al., 1993; Huxley and Curry, 1987) are performed by perfusing an inert, fluorescent tracer molecule and measuring transport into the ECM (FIG. 5). The permeability coefficient is determined from the time dependent permeation of the fluorescent tracer molecule across the endothelium. (D3: Ps approximately $1.9 \times 10^{-5}$ cm s$^{-1}$).

Example 8

Protein Expression

Protein expression of the vessels can be characterized using immunofluorescence microscopy and confocal microscopy. High resolution, wide-field images of various markers can be obtained using standard immunofluorescence techniques. Artificial brain capillaries can be imaged for the endothelial cell markers VE-cadherin, and vonWillebrand factor (vWF), the tight junction proteins occludin, claudin-5, and ZO-1, as well as the GLUT-1 glucose transporter and the P-glycoprotein (Pgp) efflux transporter. The uniformity of extracellular protein deposition by immunostaining for basement membrane proteins such as collagen IV and laminin can also be imaged (Vlodaysky et al., 1980).

Figure 6:
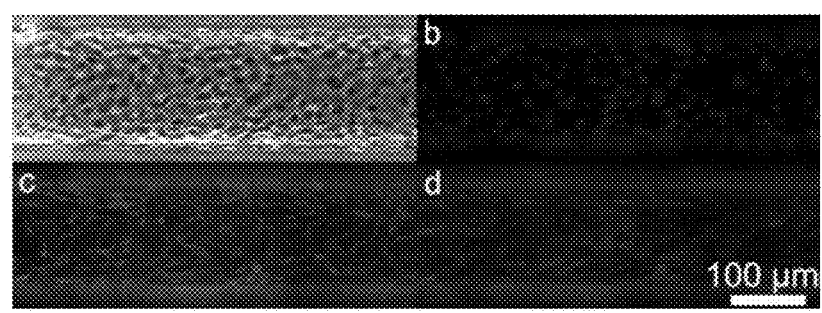

FIG. 6 shows a wide-field epifluorescence image of a presently disclosed artificial vessel with a confluent monolayer of D3 brain capillary endothelial cells surrounded by a collagen matrix as seen by phase contrast (a), DAPI nuclear stain (b), VE-cadherin junctional immunostain (c), and F-actin phallotoxin stain (d).

Example 9

Summary

An in vitro model system of the BBB is key to future advances in BBB research and therapies. It allows new insight into the structure and function of the BBB and allows fundamental studies of the effects of disrupting or compromising the BBB, e.g., through trauma or exposure to electromagnetic radiation. In addition, it allows the screening of drugs used to treat peripheral disorders that can penetrate the BBB and lead to undesirable side effects, such as drowsiness. Further, it allows drug discovery and drug delivery strategies for the treatment of CNS diseases. Also, it allows the development of therapies to repair the BBB following disease or trauma.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Abbott, N. J., Patabendige, A. A., Dolman, D. E., Yusof, S. R. & Begley, D. J. Structure and function of the blood-brain barrier. Neurobiol Dis 37, 13-25, doi:S0969-9961(09)00208-3 [pii] 10.1016/j.nbd.2009.07.030 (2010).

Neuwelt, E. A. et al. Engaging neuroscience to advance translational research in brain barrier biology. Nat Rev Neurosci 12, 169-182, doi:nrn2995 [pii] 10.1038/nrn2995 (2011).

Cecchelli, R. et al. Modelling of the blood-brain barrier in drug discovery and development. Nat Rev Drug Discov 6, 650-661 (2007).

Neuwelt, E. et al. Strategies to advance translational research into brain barriers. Lancet Neurol 7, 84-96 (2008).

Hawkins, B. T. & Davis, T. P. The blood-brain barrier/neurovascular unit in health and disease. Pharmacological Reviews 57, 173-185, doi:Doi 10.1124/Pr.57.2.4 (2005).

Begley, D. J. & Brightman, M. W. in Progress in Drug Research Vol. 61 (ed L. Prokai and K. Prokai-Tatrai) 39-78 (Birkhauser Verlag, 2003).

Ohtsuki, S. & Terasaki, T. Contribution of carrier-mediated transport systems to the blood-brain barrier as a supporting and protecting interface for the brain; Importance for CNS drug discovery and development. Pharmaceut Res 24, 1745-1758, doi:Doi 10.1007/S11095-007-9374-5 (2007).

Ueno, M. Mechanisms of the Penetration of Blood-Borne Substances into the Brain. Curr Neuropharmacol 7, 142-149 (2009).

Hartz, A. M. & Bauer, B. ABC transporters in the CNS—an inventory. Curr Pharm Biotechnol 12, 656-673, doi:BSP/CPB/E-Pub/00032-12-3 [pii] (2011).

Hawkins, R. A., Peterson, D. R. & Vina, J. R. The complementary membranes forming the blood-brain barrier. IUBMB Life 54, 101-107, doi:10.1080/15216540214541 (2002).

Chishty, M., Reichel, A., Siva, J., Abbott, N. J. & Begley, D. J. Affinity for the P-glycoprotein efflux pump at the blood-brain barrier may explain the lack of CNS side-effects of modern antihistamines. J Drug Target 9, 223-228 (2001).

Demeule, M. et al. Drug transport to the brain: Key roles for the efflux pump P-glycoprotein in the blood-brain barrier. Vasc Pharmacol 38, 339-348, doi:Pii 51537-1891(02)00201-X (2002).

Debault, L. E. & Cancilla, P. A. Gamma-Glutamyl-Transferase Transpeptidase in Isolated Brain Endothelial-Cells—Induction by Glial-Cells Invitro. Science 207, 653-655 (1980).

Janzer, R. C. & Raff, M. C. Astrocytes induce blood brain barrier properties in endothelial cells. Nature 325, 253-257 (1987).

Abbott, N. J. Astrocyte-endothelial interactions and blood-brain barrier permeability. J Anat 200, 629-638 (2002).

Abbott, N. J., Ronnback, L. & Hansson, E. Astrocyte-endothelial interactions at the blood-brain barrier. Nat Rev Neurosci 7, 41-53 (2006).

Haseloff, R. F., Blasig, I. E., Bauer, H. C. & Bauer, H. In search of the astrocytic factor(s) modulating blood-brain barrier functions in brain capillary endothelial cells in vitro. Cell Mol Neurobiol 25, 25-39 (2005).

Armulik, A., Abramsson, A. & Betsholtz, C. Endothelial/pericyte interactions. Circ Res 97, 512-523, doi:97/6/512 (2005).

Hammes, H. P. et al. Pericytes and the pathogenesis of diabetic retinopathy. Diabetes 51, 3107-3112 (2002).

Hellstrom, M. et al. Lack of pericytes leads to endothelial hyperplasia and abnormal vascular morphogenesis. Journal of Cell Biology 153, 543-553 (2001).

Fisher, M. Pericyte signaling in the neurovascular unit. Stroke 40, S13-15, doi:STROKEAHA.108.533117 (2009).

Bell, R. D. et al. Pericytes control key neurovascular functions and neuronal phenotype in the adult brain and during brain aging. Neuron 68, 409-427, doi:S0896-6273(10)00824-X (2010).

Armulik, A. et al. Pericytes regulate the blood-brain barrier. Nature 468, 557-561, doi:nature09522 (2010).

Daneman, R., Zhou, L., Kebede, A. A. & Barres, B. A. Pericytes are required for blood-brain barrier integrity during embryogenesis. Nature 468, 562-566, doi:Doi 10.1038/Nature 09513 (2010).

Winkler, E. A., Bell, R. D. & Zlokovic, B. V. Central nervous system pericytes in health and disease. Nature Neuroscience 14, 1398-1405, doi:Doi 10.1038/Nn.2946 (2011).

Bonkowski, D., Katyshev, V., Balabanov, R. D., Borisov, A. & Dore-Duffy, P. The CNS microvascular pericyte: pericyte-astrocyte crosstalk in the regulation of tissue survival. Fluids Barriers CNS 8, 8, doi:2045-8118-8-8 (2011).

Tilling, T. et al. Expression and adhesive properties of basement membrane proteins in cerebral capillary endothelial cell cultures. Cell Tissue Res 310, 19-29, doi:10.1007/s00441-002-0604-1 (2002).

Hartmann, C., Zozulya, A., Wegener, J. & Galla, H. J. The impact of glia-derived extracellular matrices on the barrier function of cerebral endothelial cells: an in vitro study. Exp Cell Res 313, 1318-1325, doi:S0014-4827(07)00044-4 (2007)

Cunningham, L. A., Wetzel, M. & Rosenberg, G. A. Multiple roles for MMPs and TIMPs in cerebral ischemia. Glia 50, 329-339, doi:10.1002/glia.20169 (2005).

Tarbell, J. M. Shear stress and the endothelial transport barrier. Cardiovasc Res 87, 320-330, doi:cvq146 (2010).

Krizanac-Bengez, L., Mayberg, M. R. & Janigro, D. The cerebral vasculature as a therapeutic target for neurological disorders and the role of shear stress in vascular homeostatis and pathophysiology. Neurol Res 26, 846-853, doi:Doi 10.1179/016164104x3789 (2004).

Cucullo, L., Hossain, M., Puvenna, V., Marchi, N. & Janigro, D. The role of shear stress in blood-brain barrier endothelial physiology. BMC Neuroscience 12, 10.1186/1471-2202-1112-1140 (2011).

Pardridge, W. M. Blood-brain barrier drug targeting: the future of brain drug development. Mol Intery 3, 90-105 (2003).

Pardridge, W. M. The blood-brain barrier: bottleneck in brain drug development. NeuroRx 2, 3-14 (2005).

Pardridge, W. M. Molecular Trojan horses for blood-brain barrier drug delivery. Curr Opin Pharmacol 6, 494-500 (2006).

Pardridge, W. M. Biopharmaceutical drug targeting to the brain. J Drug Target 18, 157-167, doi:Doi 10.3109/10611860903548354 (2010).

Pardridge, W. M. Re-engineering biopharmaceuticals for delivery to brain with molecular Trojan horses. Bioconjugate Chem 19, 1327-1338, doi:Doi 10.1021/Bc800148t (2008).

thepharmaletter. Global CNS market set to decline, but will see launch of multiple anti-Alzheimer's drugs in Japan. (2010).

Bourne-Partners. CNS Market Outlook. (Bourne Capital Partners, Healthcare Merchant Banking and Financial Advisory, 2010).

Engelhardt, B. Immune cell entry into the central nervous system: Involvement of adhesion molecules and chemokines. J Neurol Sci 274, 23-26, doi:Doi 10.1016/J.Jns.2008.05.019 (2008).

Engelhardt, B. The blood-central nervous system barriers actively control immune cell entry into the central nervous system. Curr Pharm Design 14, 1555-1565 (2008).

Zlokovic, B. V. Neurovascular mechanisms of Alzheimer's neurodegeneration. Trends Neurosci 28, 202-208, doi: S0166-2236(05)00045-7 (2005).

Kalaria, R. N. The blood-brain barrier and cerebrovascular pathology in Alzheimer's disease. Ann N Y Acad Sci 893, 113-125 (1999).

Zipser, B. D. et al. Microvascular injury and blood-brain barrier leakage in Alzheimer's disease. Neurobiology of Aging 28, 977-986, doi:S0197-4580(06)00175-8 (2007).

Meyer, E. P., Ulmann-Schuler, A., Staufenbiel, M. & Krucker, T. Altered morphology and 3D architecture of brain vasculature in a mouse model for Alzheimer's disease. P Natl Acad Sci USA 105, 3587-3592, doi:Doi 10.1073/Pnas.0709788105 (2008).

Hartz, A. M., Miller, D. S. & Bauer, B. Restoring blood-brain barrier P-glycoprotein reduces brain amyloid-beta in a mouse model of Alzheimer's disease. Mol Pharmacol 77, 715-723, doi:10.1124/mol.109.061754 (2010).

Desai, B. S., Monahan, A. J., Carvey, P. M. & Hendey, B. Blood-brain barrier pathology in Alzheimer's and Parkinson's disease: implications for drug therapy. Cell Transplant 16, 285-299 (2007).

Zhong, Z. et al. ALS-causing SOD1 mutants generate vascular changes prior to motor neuron degeneration. Nat Neurosci 11, 420-422, doi:nn2073 (2008).

Bartels, A. L. et al. Decreased blood-brain barrier P-glycoprotein function in the progression of Parkinson's disease, PSP and MSA. J Neural Transm 115, 1001-1009, doi: 10.1007/s00702-008-0030-y (2008).

Kortekaas, R. et al. Blood-brain barrier dysfunction in parkinsonian midbrain in vivo. Ann Neurol 57, 176-179, doi:10.1002/ana.20369 (2005).

Moskowitz, M. A., Lo, E. H. & Iadecola, C. The science of stroke: mechanisms in search of treatments. Neuron 67, 181-198, doi:S0896-6273(10)00540-4 (2010).

Belayev, L., Busto, R., Zhao, W. & Ginsberg, M. D. Quantitative evaluation of blood-brain barrier permeability following middle cerebral artery occlusion in rats. Brain Res 739, 88-96, doi:S0006-8993(96)00815-3 [pii] (1996).

Lo, E. H., Dalkara, T. & Moskowitz, M. A. Mechanisms, challenges and opportunities in stroke. Nat Rev Neurosci 4, 399-415, doi:10.1038/nrn1106 nrn1106 [pii] (2003).

Lippoldt, A. et al. Structural alterations of tight junctions are associated with loss of polarity in stroke-prone spontaneously hypertensive rat blood-brain barrier endothelial cells. Brain Res 885, 251-261 (2000).

del Zoppo, G. J. The neurovascular unit in the setting of stroke. J Intern Med 267, 156-171, doi:JIM2199 (2010).

Remy, S. & Beck, H. Molecular and cellular mechanisms of pharmacoresistance in epilepsy. Brain 129, 18-35, doi: awh682 (2006).

Oby, E. & Janigro, D. The blood-brain barrier and epilepsy. Epilepsia 47, 1761-1774, doi:EPI817 (2006).

Seiffert, E. et al. Lasting blood-brain barrier disruption induces epileptic focus in the rat somatosensory cortex. Journal of Neuroscience 24, 7829-7836, doi:10.1523/JNEUROSCI.1751-04.2004 24/36/7829 [pii] (2004).

Berger, J. R. & Avison, M. The blood brain barrier in HIV infection. Front Biosci 9, 2680-2685, doi:1427 (2004).

Dallasta, L. M. et al. Blood-brain barrier tight junction disruption in human immunodeficiency virus-1 encephalitis. Am J Pathol 155, 1915-1927, doi:S0002-9440(10)65511-3 (1999).

Persidsky, Y. et al. Rho-mediated regulation of tight junctions during monocyte migration across the blood-brain barrier in HIV-1 encephalitis (HIVE). Blood 107, 4770-4780, doi:2005-11-4721 (2006).

Uchiyama, S. et al. The surface-anchored NanA protein promotes pneumococcal brain endothelial cell invasion. J Exp Med 206, 1845-1852, doi:jem.20090386 (2009).

Minagar, A. & Alexander, J. S. Blood-brain barrier disruption in multiple sclerosis. Mult Scler 9, 540-549 (2003).

McQuaid, S., Cunnea, P., McMahon, J. & Fitzgerald, U. The effects of blood-brain barrier disruption on glial cell function in multiple sclerosis. Biochem Soc Trans 37, 329-331, doi:BST0370329 (2009).

Gold, R., Linington, C. & Lassmann, H. Understanding pathogenesis and therapy of multiple sclerosis via animal models: 70 years of merits and culprits in experimental autoimmune encephalomyelitis research. Brain 129, 1953-1971, doi:awl075 (2006).

Waubant, E. Biomarkers indicative of blood-brain barrier disruption in multiple sclerosis. Dis Markers 22, 235-244 (2006).

Kermode, A. G. et al. Breakdown of the Blood-Brain-Barrier Precedes Symptoms and Other Mri Signs of New Lesions in Multiple-Sclerosis—Pathogenetic and Clinical Implications. Brain 113, 1477-1489 (1990).

Bronger, H. et al. ABCC drug efflux pumps and organic anion uptake transporters in human gliomas and the blood-tumor barrier. Cancer Res 65, 11419-11428, doi:65/24/11419 (2005).

Papadopoulos, M. C. et al. Molecular mechanisms of brain tumor edema. Neuroscience 129, 1011-1020, doi: S030645220400418X (2004).

Davies, D. C. Blood-brain barrier breakdown in septic encephalopathy and brain tumours. J Anat 200, 639-646 (2002).

Stahel, P. F. et al. Experimental closed head injury: analysis of neurological outcome, blood-brain barrier dysfunction, intracranial neutrophil infiltration, and neuronal cell death in mice deficient in genes for pro-inflammatory cytokines. J Cereb Blood Flow Metab 20, 369-380, doi: 10.1097/00004647-200002000-00019 (2000).

Kim, J. V. & Dustin, M. L. Innate response to focal necrotic injury inside the blood-brain barrier. J Immunol 177, 5269-5277 (2006).

Shlosberg, D., Benifla, M., Kaufer, D. & Friedman, A. Blood-brain barrier breakdown as a therapeutic target in traumatic brain injury. Nat Rev Neurol 6, 393-403, doi:Doi 10.1038/Nrneurol.2010.74 (2010).

Nakagawa, S. et al. A new blood-brain barrier model using primary rat brain endothelial cells, pericytes and astrocytes. Neurochem Int 54, 253-263, doi:Doi 10.1016/J.Neuint.2008.12.002 (2009).

Zozulya, A., Weidenfeller, C. & Galla, H. J. Pericyte-endothelial cell interaction increases MMP-9 secretion at the blood-brain barrier in vitro. Brain Res 1189, 1-11, doi: 10.1016/j.brainres.2007.10.099 (2008).

Weidenfeller, C., Svendsen, C. N. & Shusta, E. V. Differentiating embryonic neural progenitor cells induce blood-brain barrier properties. J Neurochem 101, 555-565, doi: JNC4394 (2007).

Tilling, T., Korte, D., Hoheisel, D. & Galla, H. J. Basement membrane proteins influence brain capillary endothelial barrier function in vitro. J Neurochem 71, 1151-1157 (1998).

Rubin, L. L. et al. A Cell-Culture Model of the Blood-Brain-Barrier. Journal of Cell Biology 115, 1725-1735 (1991).

Bickel, U. How to measure drug transport across the blood brain barrier. NeuroRX 2, 15-26 (2005).

Ma, S. H., Lepak, L. A., Hussain, R. J., Shain, W. & Shuler, M. L. An endothelial and astrocyte co-culture model of the blood-brain barrier utilizing an ultra-thin, nanofabricated silicon nitride membrane. Lab Chip 5, 74-85 (2005).

Siddharthan, V., Kim, Y. V., Liu, S. & Kim, K. S. Human astrocytes/astrocyte-conditioned medium and shear stress enhance the barrier properties of human brain microvascular endothelial cells. Brain Research 1147, 39-50, doi:Doi 10.1016/J.Brainres.2007.02.029 (2007).

Lundquist, S. & Renftel, M. The use of in vitro cell culture models for mechanistic studies and as permeability screens for the blood-brain barrier in the pharmaceutical industry—Background and current status in the drug discovery process. Vasc Pharmacol 38, 355-364 (2002).

Lundquist, S. et al. Prediction of drug transport through the blood-brain barrier in vivo: A comparison between two in vitro cell models. Pharmaceut Res 19, 976-981 (2002).

Stanness, K. A. et al. Morphological and functional characterization of an in vitro blood-brain barrier model. Brain research 771, 329-342 (1997).

Cucullo, L. et al. Development of a humanized in vitro blood-brain barrier model to screen for brain penetration of antiepileptic drugs. Epilepsia 48, 505-516, doi:10.1111/j.1528-1167.2006.00960.x (2007).

Griffith, L. G. & Swartz, M. A. Capturing complex 3D tissue physiology in vitro. Nature reviews. Molecular cell biology 7, 211-224, doi:10.1038/nrm1858 (2006).

Turitto, V. T. Blood viscosity, mass transport, and thrombogenesis. Prog Hemost Thromb 6, 139-177 (1982).

Armstrong, J. K., Wenby, R. B., Meiselman, H. J. & Fisher, T. C. The hydrodynamic radii of macromolecules and their effect on red blood cell aggregation. Biophys J 87, 4259-4270, doi:Doi 10.1529/Biophysj.104.047746 (2004).

Bouis, D., Hospers, G. A., Meijer, C., Molema, G. & Mulder, N. H. Endothelium in vitro: a review of human vascular endothelial cell lines for blood vessel-related research. Angiogenesis 4, 91-102 (2001).

Poller, B. et al. The human brain endothelial cell line hCMEC/D3 as a human blood-brain barrier model for drug transport studies. Journal of neurochemistry 107, 1358-1368 (2008).

Weksler, B. B. et al. Blood-brain barrier-specific properties of a human adult brain endothelial cell line. Faseb J 19, 1872-1874, doi:10.1096/fj.04-3458fje (2005).

Hawkins, B. T. & Davis, T. P. The blood-brain barrier/neurovascular unit in health and disease. Pharmacological reviews 57, 173-185, doi:10.1124/pr.57.2.4 (2005).

Hirst, D. G., Denekamp, J. & Hobson, B. Proliferation Studies of the Endothelial and Smooth-Muscle Cells of the Mouse Mesentery after Irradiation. Cell Tissue Kinet 13, 91-104 (1980).

Wright, H. P. Mitosis Patterns in Aortic Endothelium. Atherosclerosis 15, 93-& (1972).

Chrobak, K. M., Potter, D. R. & Tien, J. Formation of perfused, functional microvascular tubes in vitro. Microvasc Res 71, 185-196, doi:10.1016/j.mvr.2006.02.005 (2006).

Yuan, Y., Chilian, W. M., Granger, H. J. & Zawieja, D. C. Permeability to albumin in isolated coronary venules. Am J Physiol 265, H543-552 (1993).

Huxley, V. H., Curry, F. E. & Adamson, R. H. Quantitative Fluorescence Microscopy on Single Capillaries—Alpha-Lactalbumin Transport. Am J Physiol 252, H188-H197 (1987).

Price, G. M., Chrobak, K. M. & Tien, J. Effect of cyclic AMP on barrier function of human lymphatic microvascular tubes. Microvasc Res 76, 46-51, doi:DOI 10.1016/j.mvr.2008.02.003 (2008).

Vlodaysky, I., Lui, G. M. & Gospodarowicz, D. Morphological appearance, growth behavior and migratory activity of human tumor cells maintained on extracellular matrix versus plastic. Cell 19, 607-616 (1980).

Zheng, Y. et al. In vitro microvessels for the study of angiogenesis and thrombosis. Proc Natl Acad Sci USA 109, 9342-9347, doi:10.1073/pnas.1201240109 (2012).

Wong, K.H.K., Truslow, J.G., and Tien, J. The role of cyclic AMP in normalizing the function of engineered human blood microvessels in microfluidic collagen gels. Biomaterials 31(17), 4706-4714 (2010).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for fabricating an artificial blood-brain barrier (BBB) comprising a template comprising an inlet and outlet, wherein the template contains a three-dimensional (3D) extracellular matrix (ECM) comprising at least one artificial vessel embedded therein, wherein the at least one embedded artificial vessel has an inner surface defined by a confluent monolayer of brain microvascular endothelial cells, and wherein the at least one artificial vessel is in fluid communication with the inlet and outlet of the template, the method comprising:

(a) providing a mold adapted to form the template, wherein the mold comprises one or more channels configured to define one or more walls of the template;

(b) disposing a thermoplastic material into the mold and curing the thermoplastic material to form the template, wherein the template has an upstream end and a downstream end;

(c) forming an inlet in the upstream end of the template for an inlet port and an outlet in the downstream end of the template for an outlet port;

(d) inserting a rod extending from the inlet in the upstream end of the template to the outlet in the downstream end of the template, wherein the rod is aligned with the inlet and outlet ports;

(e) disposing a material comprising the ECM into the template;

(f) allowing the material comprising the ECM to gel, then removing the rod to form at least one embedded artificial vessel in the ECM; and (g) perfusing the at least one embedded artificial vessel in the ECM with brain microvascular endothelial cells to line an inner surface of the at least one embedded artificial vessel with a confluent monolayer of brain microvascular endothelial cells.

2. The method of claim 1, further comprising modifying one or more external surfaces of the rod with a surfactant prior to inserting the rod to extend from the inlet in the upstream end of the template to the outlet in the downstream end of the template.

3. The method of claim 1, further comprising oxidizing the template.

4. The method of claim 3, comprising oxidizing the template with plasma oxidation.

5. The method of claim 1, further comprising modifying one or more internal surfaces of the template with a silane compound having an epoxide group.

6. The method of claim 5, wherein the silane compound having an epoxide group comprises (3-glycidyloxypropyl) trimethoxysilane.

7. The method of claim 1, further comprising gelling the material comprising the ECM in the presence of ammonia vapor.

8. The method of claim 1, further comprising bonding the template to a glass surface.

9. The method of claim 1, further comprising crosslinking the material comprising the ECM.

10. The method of claim 9, wherein the crosslinking includes the formation of covalent amide bonds.

11. The method of claim 10, wherein the covalent amide bonds are formed via the addition of bis[sulfosuccinimidyl] suberate.

12. The method of claim 1, further comprising operationally connecting at least one component selected from the group consisting of a bubble trap, a reservoir, a pressure relief valve, and combinations thereof, to the at least one artificial vessel.

* * * * *